United States Patent [19]
Rainville et al.

[11] Patent Number: 6,080,843
[45] Date of Patent: Jun. 27, 2000

[54] GELATIN AND METHOD OF MANUFACTURE

[75] Inventors: Robert F. Rainville, North Andover, Mass.; Anne G. Rowlands, Honeoye Falls; Deborah J. Burrows, Rochester, both of N.Y.; Peter Noble, Macclesfield, United Kingdom

[73] Assignee: Eastman Kodak Company, Rochester, N.Y.

[21] Appl. No.: 09/185,441

[22] Filed: Nov. 3, 1998

[51] Int. Cl.[7] .............................. C07K 1/00; C07K 14/00
[52] U.S. Cl. ............................................. 530/355; 435/273
[58] Field of Search .................................. 530/354, 355; 435/265, 273

[56] References Cited

U.S. PATENT DOCUMENTS 5,919,906 7/1999 Rowlands et al. ...................... 530/354

Primary Examiner—Nathan M. Nutter
Attorney, Agent, or Firm—Carl F. Ruoff; Doreen M. Wells

[57] ABSTRACT

The present invention is a gelatin composed of a high molecular weight fraction (>250,000) of from 0 to 25 wt %, a beta fraction (150,000–250,000) of from 0 to 20 wt % and an alpha fraction (50,000–150,000) of from 15 to 55 wt %. The gelatin has a Gel strength of from 150 to 350 g Bloom and a concentration of protease of greater than 10 ppb and an absorbance of at least 0.069 at 420 nm. The present invention also is a process for the manufacture of photographic gelatin. The process begins by liquefying or slurrying the residual ossein. Protease is added to the gelatin solution or ossein slurry to a concentration of at least 10 ppb to form a mixture. The mixture is reacted for a time sufficient to achieve a viscosity of less than 9 cps (6.16% gel concentration at 104° F.) and the protease is inactivated. The mixture is clarified to form a gelatin solution wherein the gelatin is of high quality.

9 Claims, No Drawings

GELATIN AND METHOD OF MANUFACTURE

CROSS REFERENCE TO RELATED APPLICATIONS

This application relates to commonly assigned copending application Ser. No. 09/186,433 and now U.S. Pat. No. 5,919,906 filed simultaneously herewith incorporated by reference herein. This application relates to commonly assigned copending application Ser. No. 09/185,440, filed simultaneously herewith incorporated by reference herein. This application relates to commonly assigned copending application Ser. No. 09/185,209, filed simultaneously herewith incorporated by reference herein.

FIELD OF THE INVENTION

The present invention relates to the production of gelatin. More, particularly the present invention provides a method of extracting high quality gelatin from residual ossein stock after gelatin extractions.

BACKGROUND OF THE INVENTION

Gelatin obtained in the later extractions (beyond 15 weight % of the bone) from an alkaline processed ossein is typically high in color (absorbance at 420 nm), low in Gel Strength, and high in viscosity. Low Gel strength limits the applicability of the gelatin in imaging, and some pharmaceutical and edible applications where enhanced setting properties of gelatin are necessary.

The extraction of gelatin from collagen-bearing materials such as ossein is typically performed in tanks with a perforated false bottom. The ossein rests on the false bottom in a bed and water is introduced into the bed at temperatures of from 120 to 180° F. The ossein is steeped in the heated water for one to four hours, then the gelatin solution is removed from the vessel, with the ossein retained in the vessel on the false bottom. Fresh water at a higher temperature is introduced into the vessel, and a second extraction cycle begins. In other cases, the gelatin solution is continuously drained and fresh hot water is added to the vessel in order to maintain the liquid level. A charge of ossein typically undergoes several of these extraction cycles at increasing temperatures or prolonged extraction at gradually increasing temperature. As a result of the higher extraction temperatures, and the increasing level of impurities in the remaining ossein, gelatins produced from the later extractions are less transparent and darker in color than gelatin from earlier extractions, and are less valuable for photographic purposes.

After extraction of photographic gelatin from ossein, the remaining ossein can be heated to the boiling point to solubilize the remaining gelatin. This extracted gelatin has a low Gel strength, typically 60–120 Bloom grams and is unsuitable for photographic applications.

An object of the invention is to provide a gelatin of photographic quality from the residual ossein.

Another object of the present invention is to provide a process for recovering high quality gelatin from the residual ossein.

SUMMARY OF THE INVENTION

The present invention is a gelatin composed of a high molecular weight fraction (>250,000) of from 0 to 25 weight %, a beta fraction (150,000–250,000) of from 0 to 20 weight % and an alpha fraction (50,000–150,000) of from 15 to 55 weight %. The gelatin has a Gel strength of from 150 to 350 g Bloom and a concentration of protease of greater than 10 ppb and an absorbance of at least 0.069 at 420 nm, when measured at a gel concentration of 6.16%.

The present invention also is a process for the manufacture of photographic gelatin. The process begins by liquefying or slurrying the residual ossein to obtain a gelatin mixture. Protease is added to the gelatin mixture to a concentration of about 10 ppb to form an enzyme mixture. The enzyme mixture is reacted for a time sufficient to achieve a viscosity of less than 9 cps (6.16% gel concentration at 104° F.) and the protease is inactivated. The mixture is clarified to produce photographic quality gelatin.

DETAILED DESCRIPTION OF THE INVENTION

The present invention describes a novel gelatin product produced by the enzymatic action of proteases on residual ossein from alkaline processed ossein. The gelatin described in this invention has enhanced Gel strength and reduced viscosity from typical late extraction gelatin.

The present invention is a process that partially or completely eliminates the use of high temperature (boiling) in the extraction of gelatin from residual ossein. The residual ossein can be liquefied by heating it to a temperature of at least 150° F. for a sufficient time. Alternately, the residual ossein can be finely divided to a particle size of 100 microns or less and slurried with water. The gelatin solution or slurry is cooled to a temperature less than 130° F. Protease or a proteolytic enzyme is added to the gelatin solution at a concentration of at least 10 ppb, preferably at least 1 ppm and most preferably at least 40–100 ppm to form a mixture. The mixture is reacted for a time sufficient to achieve a viscosity of less than 9 cp, preferably between 2 and 9. The protease is deactivated and the gelatin is clarified.

Typical collagen containing materials include skin, bone, and connective tissue of an animal body. Sources of animal bodies include cattle, pigs and sheep. The most preferred source for collagen for production of photographic gelatin is cattle bone. Ossein is a collagen containing material which has been degreased and demineralized.

Due to variable bond breakage during manufacture, gelatin is composed of a distribution of proteins of varying chain lengths. Aqueous size exclusion chromotagraphy provides a method of analysis for determining the gelatin molecular weight distribution. This distribution is described as containing the following fractions; high molecular weight or HMW (>250 K daltons); Beta (250–150 K daltons); Alpha (150–50 K daltons); Subalpha (50–20 K daltons); and low molecular weight or LMW (20–4 K daltons). In general, high gel strength correlates with high gelatin alpha fraction content, and high viscosity correlates with high gelatin HMW fraction content.

Enzymes are biological catalysts. Similar to traditional chemical catalysts, enzymes speed the rate of biological reactions by producing a transition state with a lower energy of activation than the uncatalyzed reaction. Unlike traditional chemical catalysts, enzymes are biological in nature. Enzymes are proteins specialized for the reactions they catalyze. In other words enzymes exhibit substrate specificity. Proteases are enzymes that catalyze the hydrolysis of peptide bonds in proteins and peptides.

Enzymes are irreverisbly inactivated by agents or processes which covalently and permanently modify the active site of the enzyme. Typically, reactions which denature proteins achieve this affect. For example extremes in pH or elevated temperatures inactivate enzymes.

Purification of enzyme extracted gelatin can be varied to achieve the desired level of microconstitutents. Filtration can be combined with deionization, oxidation, or a clarification process. The clarification process removes non-gelatin proteins and lipids through flocculation. Following purification, gelatin extractions can be blended in liquid form prior to a concentration step. The concentration step is achieved through an evaporative process. Concentrated gelatin can be used in liquid, chilled or dried form.

The gelatin containing solution is clarified by raising the pH of the solution to between 9.0 and 10.0. A sulfate salt of a divalent or trivalent cation (usually a metal) is added to the gelatin solution to reduce the pH to between 7.0 and 8.0. An acid, preferably phosphoric is added to the solution to reduce the pH to between 5.0 and 6.0. A polymeric flocculent is added to the gelatin containing solution at an amount of 5 to 15 ppm based on the volume of the gelatin solution to form a floe which is removed. Following extraction and clarification the gelatin solution is, filtered, oxidized or deionized to achieve desired levels of microconstituents, prior to concentration and drying.

The present invention is described with particular reference to the following Examples.

EXAMPLE 1

High gel strength clarified gelatin was prepared by the following procedure. Following thermal extraction of limed ossein wherein approximately 15% of the initial bone mass was extracted as gelatin, the residual ossein was heated for 3 hours at a temperature of 150° F. which resulted in a liquefied gelatin solution. The liquefied gelatin solution was pumped to a water jacketed tank maintained at 120° F. and mixed at 45 RPM. Neutrase (NOVO Chemicals), a protease, was added with rapid mixing to achieve an enzyme concentration of 100 ppm based on the dry weight of the gelatin. Viscosity was monitored to control the enzyme reaction. The enzyme was deactivated with pH adjustment to about 4.2 with phosphoric acid addition when the desired viscosity, which is dependent on the final use of the gelatin, was reached. Following enzyme treatment the resulting gelatin was clarified. The clarification procedure used included addition of lime (5–7 BE or degrees Baume) (6 degrees Baume is equivalent to 53.8 g CaO/liter) to achieve a pH of about 9.8, followed by addition of aluminum sulphate (25%) to reduce the pH to 7.5 and addition of phosphoric acid (10%) to reduce the pH to 5.2. A floating floc was formed by the addition of polyacrylamide polymer (0.1% w/v) to an aerated gelatin solution. Upon removal of the floc, the gelatin was plate and frame filtered, deionized, concentrated, pH adjusted to pH 5.75, sterilized at 285° F. and dried.

EXAMPLE 2

Following thermal extraction of limed ossein wherein approximately 15% of the initial bone mass was extracted as gelatin, the residual ossein was removed from the extraction vessel and ground to a maximum particle size of 100 micron. The finely divided ossein slurry was pumped to a water jacketed tank maintained at 130° F. and mixed at 45 RPM. Neutrase (NOVO Chemicals), a protease, was added with rapid mixing to slurry to achieve an enzyme concentration of 50 ppm on the estimated dry weight of gelatin. Viscosity was monitored to control the enzyme reaction. The enzyme was deactivated with pH adjustment to 4.2 with phosphoric acid addition when the desired viscosity, which is dependent on the final use of the gelatin, was reached. Following enzyme treatment the resulting gelatin was clarified. The clarification procedure used was the same as that used in Example 1.

Molecular weight distribution of gelatin was determined by high-performance liquid chromatography in the aqueous size exclusion mode. Gelatin samples were dissolved in the chromatographic eluent, a phosphate buffer containing sodium dodecyl sulfate. Different molecular weight fractions were separated on a Toso Haas TSK Gel size exclusion column and the effluent monitored with a UV detector set at 220 nm. Known molecular weight standards were used to prepare a calibration curve, which was constructed by plotting the log of molecular weight versus retention time. The molecular weight distribution of unknown gelatin samples were determined from the linear portion of this calibration curve.

Absorbance at 420 nm was measured using a 6.16% gel solution moisture corrected. Viscosity of 6.16% moisture corrected gelatin solutions were determined using a Brookfield viscometer. Gel strength was determined by analysis of a chilled 6.16% gel solution with a Voland-Stevens Texture Analyzer.

Example 3

Enzyme treatment of late extraction gelatin from alkaline processed ossein. A late extraction gelatin (approximately 15% previously extracted) from alkaline processed ossein was treated with 2 ppm Protex 6L (Genencor International), a protease, for varying times at 50° C. The ability of the enzyme process to enhance gel strength and vary viscosity is demonstrated below.

| Time enzyme incubation (hours) | 0 | 0.3 | 1 | 2 |
| --- | --- | --- | --- | --- |
| Molecular Weight Fractions | | | | |
| HMW | 37.71 | 33.62 | 24.97 | 16.7 |
| BETA | 18.93 | 19.31 | 19.38 | 18.4 |
| ALPHA | 33.85 | 35.74 | 39.62 | 43.36 |
| Viscosity (cps) | 12.4 | 9.57 | 7.06 | 5.41 |
| Gel Strength (g) | 224 | 235 | 241 | 242 |

EXAMPLE 4

Comparison of enzyme treated late extraction gelatin as prepared in Example 1 versus late extraction gelatin obtained without the use of protyletic enzymes. Both sample were clarified according to the procedure described in Examples 1 and 2.

This comparision is shown below.

| | CG | HGSC |
| --- | --- | --- |
| Molecular Weight Fractions | | |
| HMW | 11.84 | 13.88 |
| BETA | 13.71 | 16.6 |
| ALPHA | 35.21 | 40.07 |
| Viscosity (cps) | 3.95 | 4.92 |
| Gel Strength (g) | 122 | 232 |
| Absorbance @ 420 nm | 0.181 | 0.094 |

GC Alkaline processed late extraction clarified gelatin
HGSC Alkaline processed late extraction enzyme treated and clarified gelatin From the comparison it is apparent that the use of a protyletic enzyme to extract gelatin from residual ossein results in gelatin with higher gel strength and lower absorbance at 420 nm.

The invention has been described in detail with particular reference to certain preferred embodiments thereof, but it will be understood that variations and modifications can be effected within the spirit and scope of the invention.

What is claimed is:

1. A process for the manufacture of photographic gelatin comprising:

liquefying or slurrying residual ossein;

adding protease to the liquefied or slurried ossein at a concentration of at least 10 ppb to form a mixture;

reacting the mixture for a time sufficient to achieve a viscosity less than 9 cp;

inactivating the protease to produce gelatin in solution wherein the gelatin comprises a high molecular weight fraction (>250,000) of from 0 to 25 wt %, a beta fraction (150,000–250,000) of from 0 to 20 wt %, an alpha fraction (50,000–150,000) of from 15 to 55 wt %, and an absorbance of greater than 0.069 at 420 nm.

2. The process of claim 1 wherein the step of liquefying or slurrying the residual ossein comprises by heating the residual ossein to a temperature of at least 150° F.

3. The process of claim 1 wherein the step of liquefying or slurrying the residual ossein comprises finely dividing the residual ossein to a size less than 100 microns and slurrying the divided ossein with water.

4. The process of claim 1 further comprising clarifying the gelatin.

5. The process of claim 4 wherein the step of clarifying the gelatin comprises:

raising the pH of the gelatin solution to between 9.0 and 10.0;

adding a sulfate salt of a divalent or trivalent cation to the gelatin solution to reduce the pH of from 7.0 to 8.0;

adding an acid to the gelatin solution to reduce the pH to from 5.0 to 6.0;

adding a polymeric flocculant to the gelatin solution in an amount of about 5 to 15 ppm based on a liquid volume of the gelatin solution to produce a floc;

removing the floc from the gelatin solution; and filtering the gelatin solution.

6. The process of claim 5 wherein the acid added to the gelatin solution comprises phosphoric acid.

7. The process of claim 5 wherein the polymeric flocculant comprises polyacrylamide polymer.

8. The process of claim 5 wherein the sulfate salt comprises aluminum sulfate.

9. The process of claim 1 further comprising:

concentrating the gelatin solution.

\* \* \* \* \*